(12) United States Patent
Heim et al.

(10) Patent No.: US 8,043,551 B2
(45) Date of Patent: Oct. 25, 2011

(54) METHOD FOR PRODUCING AN AORTIC OR MITRAL HEART VALVE PROSTHESIS AND RESULTING AORTIC OR MITRAL HEART VALVE

(75) Inventors: Frédéric Heim, Didenheim (FR); Bernard Durand, Pfastatt (FR); Jean-Georges Kretz, Strasbourg (FR); Nabil Chakfe, Eschau (FR)

(73) Assignees: Universite de Haute Alsace (UHA), Mulhouse (FR); Les Hopitaux Universitaires de Strasbourg, Strasbourg (FR); Universite de Strasbourg (UDS), Strasbourg (FR)

( * ) Notice: Subject to any disclaimer, the term of this patent is extended or adjusted under 35 U.S.C. 154(b) by 1235 days.

(21) Appl. No.: 10/512,567

(22) PCT Filed: Apr. 22, 2003

(86) PCT No.: PCT/FR03/01271
§ 371 (c)(1),
(2), (4) Date: Apr. 19, 2005

(87) PCT Pub. No.: WO03/090645
PCT Pub. Date: Nov. 6, 2003

(65) Prior Publication Data
US 2005/0177227 A1      Aug. 11, 2005

(30) Foreign Application Priority Data

Apr. 23, 2002 (FR) .................................... 02 05086
Sep. 27, 2002 (FR) .................................... 02 12030

(51) Int. Cl.
*B29C 51/10* (2006.01)
*B29C 51/30* (2006.01)
*A61F 2/24* (2006.01)
*A61F 2/06* (2006.01)

(52) U.S. Cl. .................. 264/511; 264/324; 623/1.26
(58) Field of Classification Search .................. 264/572, 264/511, 324
See application file for complete search history.

(56) References Cited

U.S. PATENT DOCUMENTS

| 2,832,078 A | * | 4/1958 | Williams | 623/2.19 |
| 2,922,437 A | * | 1/1960 | Rippingille | 137/844 |
| 4,610,688 A | * | 9/1986 | Silvestrini et al. | 623/1.53 |
| 4,695,422 A | * | 9/1987 | Curro et al. | 264/504 |
| 5,500,015 A |   | 3/1996 | Deac | |
| 5,695,376 A | * | 12/1997 | Datta et al. | 442/334 |
| 5,713,953 A |   | 2/1998 | Curcio et al. | |

FOREIGN PATENT DOCUMENTS

| CH | 510 433 | | 7/1971 |
| EP | 0 331 345 | | 9/1989 |
| EP | 0 331 345 A2 | * | 9/1989 |
| FR | 2 728 457 | | 6/1996 |
| WO | 01 /52776 | | 7/2001 |

\* cited by examiner

*Primary Examiner* — Richard Crispino
*Assistant Examiner* — Patrick Butler
(74) *Attorney, Agent, or Firm* — Young & Thompson

(57) ABSTRACT

A method for producing an aortic or mitral heart valve prosthesis and the resulting aortic or mitral heart valve. The method is characterized in that it essentially consists in producing the prosthesis by shaping a textile material. The invention is more particularly applicable in the field of medicine, in particular repair surgery, and especially in heart surgery, more particularly heart prostheses.

11 Claims, 2 Drawing Sheets

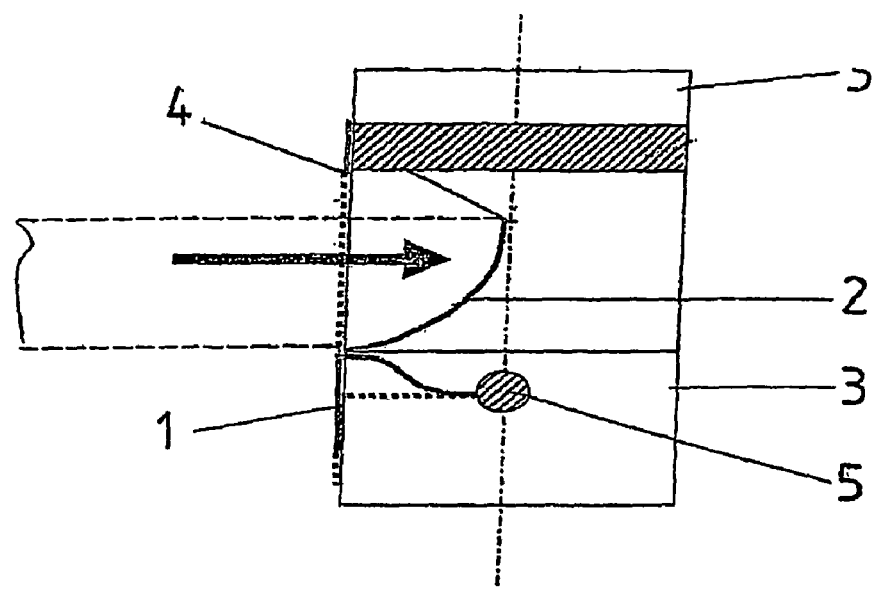
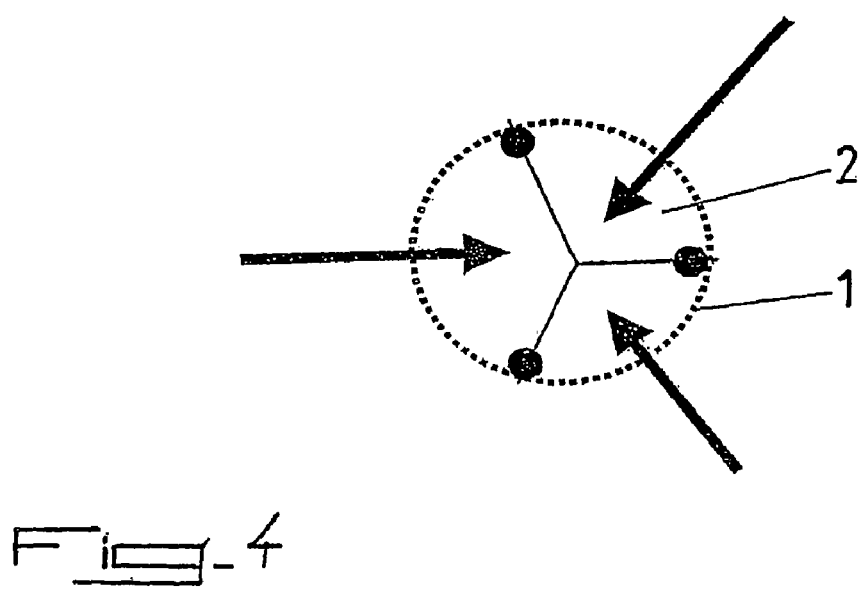

METHOD FOR PRODUCING AN AORTIC OR MITRAL HEART VALVE PROSTHESIS AND RESULTING AORTIC OR MITRAL HEART VALVE

The present invention relates to the field of medicine, in particular reparative surgery, and especially cardiac surgery, more particularly cardiac prostheses, and has for its object a process for the production of an aortic or mitral cardiac valve prosthesis.

The invention also has for its object an aortic or nitral cardiac valve prosthesis obtained by practice of this process.

The implantation of aortic cardiac valve prostheses is generally necessary to overcome insufficiencies due to degeneration of said valve, this more particularly for reasons of calcification due to abnormal impregnation of the tissues by calcium salts following degeneration of the collagen fibers. As a result, there is a rigidification of the tissue of the valve and a loss of flexibility during movement of the flaps under the action of the cardiac pump. These flaps forming the valve are thus subjected to a continuous opening and closing movement of the aorta at a speed corresponding to the cardiac pulsation rhythm, such that any rigidification of the tissue constituting them gives rise inevitably to wear accelerated by fatigue.

This wear of the cardiac valve will have two types of consequences, namely, a valve symphysis creating an aortic constriction resulting in an obstacle to evacuation of the left ventricle and a destruction of the valves creating a diastolic reflux toward the left ventricle. These two effects lead to cardiac insufficiency.

To repair the insufficiency due to deterioration of the cardiac valve, the first processes used to construct mechanical prosthetic valves consisted in making them in the form of a ball of biocompatible material lodged in a retention cage forming simultaneously a sealed seat on the side turned toward the cardiac muscle, these valves being mounted at the outlet of the cardiac muscle, at the end of the artery comprising the sinuses for reflux of the blood flow during closure of the valve.

At present, the mechanical valves are constructed with one or several flaps mounted on eccentric axes secured to a securement seat on the cardiac muscle.

These known mechanical valves have excellent reliability of operation, but however they give rise to turbulence which can be the origin of a phenomenon risking causing thromboses, such that their implantation requires for the patient thus provided the lifetime consumption of anti-coagulant medical products.

To avoid these drawbacks, there has been proposed a use of bioprostheses, which is to say prostheses made from human organic tissues (homografts) or else porcine prostheses, which is to say porcine cardiac valves.

The biological sheets of such prostheses are generally very well supported by grafting. However, because of their construction from organic tissues, they are subject to aging and to natural degeneration. These biological sheets are mounted on a seat which generates a hemodynamic brake to ejection.

Finally, it has also been proposed to make valve prostheses of synthetic material, particularly shaped polyurethane or silicon. However, these valves have problems of resistance in fatigue, with risk of breaking at the flexure zones.

The present invention has for its object to overcome these drawbacks by providing a process for the production of an aortic or mitral cardiac valve prosthesis and a cardiac valve prosthesis thus obtained, permitting obtaining a perfectly biocompatible prosthesis of excellent resistance to aging.

To this end, the process for production of an aortic or mitral cardiac valve prosthesis is characterized in that it consists essentially in making said prosthesis by shaping a textile material.

The invention also has for its object an aortic or mitral cardiac valve prosthesis, obtained by the practice of this process, characterized in that it is essentially constituted by a textile material.

The invention will be better understood from the following description, which relates to a preferred embodiment, given by way of non-limiting example, and explained with reference to the accompanying schematic drawings, in which:

FIG. 3 is a side elevational view, on a larger scale, explaining the sheathing operation, and FIG. 4 is a plan view corresponding to FIG. 3 and showing schematically the three flaps of the prosthesis and the directions of sheathing.

Figure 1:
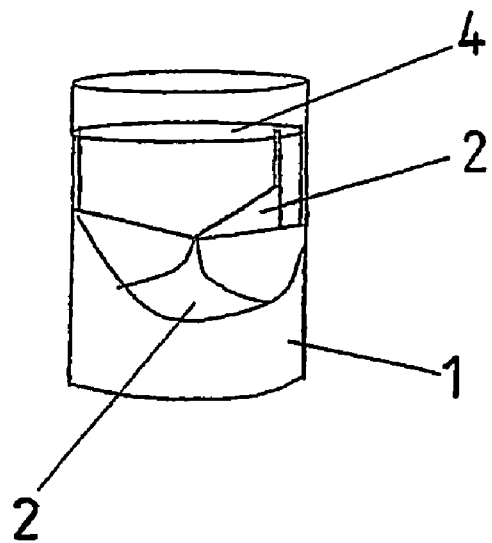
FIG. 1 is a perspective view of the prosthesis according to the invention.

FIG. 1 of the accompanying drawings shows a cardiac valve prosthesis 1 essentially constituted by three flaps 2.

This aortic or mitral cardiac valve prosthesis is preferably made, according to the invention, by a process which consists essentially in making said prosthesis by shaping a textile material.

According to one characteristic of the invention, the flaps 2 of the cardiac valve prosthesis 1 are preferably made by shaping a textile membrane. This textile membrane is a membrane of the type selected from the group comprised by the following modes of assembly: woven, non-woven in the form of assembled fibers, non-woven obtained by autofibrillation of a membrane by drawing and knitting.

The shaping is carried out according to an operation selected from the following group: concentric sheathing, knitting in three dimensions, flat sheathing, cutting out by bending and securement and, if desired, thermofixing, preliminary mechanical deformation and application, at the deformations, of a heat exchange fluid, application against a counterform by the effect of suction through said counterform and thermofixation by supplying hot air or gas drawn through the textile member on the counterform, heat exchange fluid pressing the textile member against a counterform.

Figure 2:
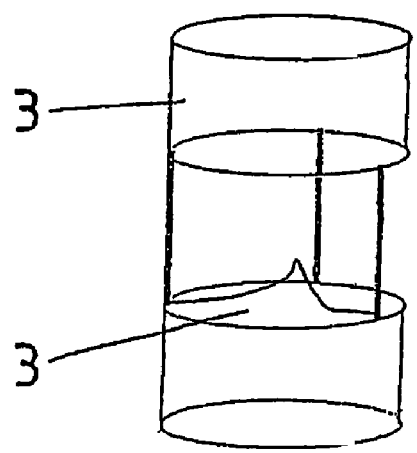
FIG. 2 is a perspective view of the sheathing support of the process according to FIG. 1.

According to a first embodiment of the invention and as shown more particularly in FIGS. 2 to 4 of the accompanying drawings, the shaping of the flaps 2 can be carried out by a tubular element 1 of a textile membrane by sheathing of three flaps 2 of identical surfaces on a shaping member 3 reproducing the geometry of the flaps 2 of a cardiac valve in the closed position of the artery, with preliminary cutting out of said tubular element 1 in cylindrical segments 4 extending between the radii of said flaps 2. To this end, the tubular element 1 is held firmly above the segments 4 forming the object of the preliminary cutting out and can slide on the lower portion of the shaped member 3 reproducing the geometry of the flaps 2 to form said flaps without plastic elongation deformation of the fibers, but with reduced deformation of the membrane or the meshes of the cloth. The cutout edges of the flaps 2 are then provided with a protection means and joining means between the flaps in the closed position of the valve. As a function of the material used for the textile membrane constituting the tubular element 1, there is then carried out if desired a thermosecurement of said membrane thus deformed, by passage through an oven at a temperature slightly greater than the vitreous transition temperature, then, after eventual cooling, the valve prosthesis thus obtained is removed from the shaping member 3.

The textile material used is preferably constituted by fibers of polyester or of polytetrafluoroethylene taken alone or in mixture or else by an autofibrilated membrane by drawing of polytetrafluoroethylene.

In the case of the use of polyester fibers mixed or not with fibers of polytetrafluoroethylene, it is necessary to carry out a thermofixation in an oven, this at a temperature of the order of 120° C., the vitreous transition temperature of the fibers being of the order of 80° C. in open air for polyester.

On the contrary, in the case of the use of a membrane autofibrilated by drawing polytetrafluoroethylene, the sheathing successive to cutting out of the segments between the radii permits obtaining flaps 2 slightly in the form of pockets by permanent plastic deformation, without requiring any ultimate fixation treatment.

The result is the obtention of flaps 2 having a geometry identical to that of the flaps of a human valve, permitting respecting hemodynamism.

Preferably, each flap 2 extends over a circular segment having an opening angle of 120° about the periphery, such that the free edge of each pocket delimited by each flap 2 will have a length, corresponding to twice the length of the radius of the flap, which will be slightly less than that defined by said angle of opening about the perimeter, a length which will correspond to twice the radius multiplied by n and divided by three. The result is that the edges of the flaps have a tendency, in cooperation with the circular segment delimiting each flap, to deform said flaps in the form of a pocket decreasing upwardly in the direction of the arterial sinus, which permits guaranteeing one of the conditions of closure of the valve during the diastolic phase.

According to one characteristic of the invention, the preliminary cutting out of the tubular element 1 on the cylindrical segments 4 extending between the radii of said flaps 2 is preferably carried out for each flap 2 by means of a cutting device (not shown) with a blade, or heating, or other sectioning of the tubular element of textile material 1 over all the length of the segment with positioning of said device slightly in front of the beginning of the simultaneous concentric sheathing of the three flaps 2 on the forming member 3.

To secure holding of the tubular element 1 above the segments 4 during preliminary cutting out and concentric sheathing can be ensured in a known manner by a simple clamp not described in detail. This holding can permit ensuring on the one hand the creation, in combination with the sheathing support 3, of cutting ridges coacting with the corresponding cutting device and, on the other hand, the blocking of the cloth over all the perimeter of the upper portion of said sheathing support, such that during concentric sheathing, the tubular element of textile material cannot move downwardly in the direction of the sheathing dies, whilst the portion of the tubular element of textile material extending over the lower portion of the sheathing support 3 reproducing the geometry of the flaps 2 can slide over said lower portion.

This idea of holding the textile material on the upper portion and the possibility of sliding over the lower portion is shown more particularly in FIG. 3 of the accompanying drawings. The result is that the deformation of the textile material at the sheathing takes place in a perfectly balanced manner over all the sheathed zones, the filling of the cavities of the lower portion of the sheathing support 3 taking place essentially by sliding of the textile material, on the one hand, between the region in which it is cut off, and the upper portion of the support 3 in each segment formed between the ends of the constituent radii of the flaps 2 and, on the other hand, from the bottom of said support 3. Thus, any possibility of producing a zone of elementary mesh that is too great, hence having unbalanced sealing, is avoided, the structure of the textile material at the flaps 2 remaining very near the beginning structure of the textile material.

The drawing support structure 3 is preferably constituted by a lower cylindrical portion comprising a central portion molded with shapes corresponding to the shape of the flaps 2 to be obtained, and by an upper cylindrical portion connected to the lower portion by means of three holding rods extending between themselves at intervals of 120° and implanted in line with the junction of the radii constituting said flaps 2 with the corresponding angular segment, said upper portion having, in the direction of the lower portion, a surface which is perfectly flat and an outer edge which is preferably cutting. The height of the rods will be a function of the geometry of the pocket, formed in each flap 2, to be obtained, and, in any case, must permit optimum distribution of the deformations.

At the height of the holding rods of the sheathing support, the tubular element in textile material is not subject to cutting out, such that the sheathed member obtained has a lower portion provided with flaps 2 and prolonged downwardly by a cylindrical skirt, said cylindrical skirt with the flaps 2 being connected by wall elements of relatively small width and an upper cylindrical ring, whose height can correspond to the height of the gripping clamp of the annular element on the sheathing support 3. The width of these wall elements will be substantially equal to the diameter or to the width of the holding rods connecting the upper and lower portions of the sheathing support 3.

Moreover, the height, not only of the upper cylindrical ring but also of the lower cylindrical skirt, can be adapted as a function of needs, by cutting off a strip of textile material that is more or less great.

Preferably, the tubular element in textile material is blocked at points at three regular intervals of 120° on the lower portion of the sheathing support 3, by means of blocking means 5, such as retaining points (FIG. 3), these blocking means 5 extending in prolongation of the holding rods connecting the upper and lower portions of said sheathing support 3. The provision of these blocking means 5 permits ensuring, during the sheathing operation and partial displacement of the textile material on the lower portion of the sheathing support 3, a holding without friction of the annular tube of textile material and more particularly avoiding friction of this tube at the wall elements connecting the upper tubular ring to the lower tubular skirt constituting the valve prosthesis. Similarly, a deformation by friction of the lower tubular skirt is also avoided. As a result, the obtained valve prosthesis has not only an external surface but also an internal surface that is perfectly continuous.

According to another characteristic of the invention, the fibrous structure constituting the tubular element in textile material can be constituted, either in the form of a longitudinal strip closed on itself along a longitudinal generatrix by stitching, or in the form of a continuous tube, without stitching.

According to another characteristic of the invention, this fibrous structure can be provided with a cladding of material or inserts of material improving its surface condition or promoting the rehabilitation and/or having particular physiological properties. Thus, the fibrous structure could be provided particularly with a cladding or inserts of a medical substance that dissolves very slowly, for example to avoid the formation of clots or else a colony of endothelial cells.

Preferably, the textile material constituting the valve prosthesis according to the invention is advantageously a microporous membrane permitting a slight exchange of fluids between the two surfaces of the flaps 2.

The emplacement on the cut edges of the flaps 2 of a protective and junction means between flaps in the closed position of the valve, consists preferably essentially in a treatment of the cutoff portions of each flap 2, namely the junction radii to the corresponding circular segment, by deposition of a coating material on the cutoff ridges, in the form of pad or the like, the emplacement of such material permits on the one hand ensuring a perfect arrangement of the warp and weft filaments in the cutoff edges and avoiding their raveling and, on the other hand, forming a sealing device at the contact of the edges of the flaps 2 (between the radius), during closure of the valve at the time of diastolysis.

According to a modified embodiment of the invention, not shown in the accompanying drawings, it is also possible to make an aortic or mitral cardiac valve prosthesis essentially by carrying out a shaping by knitting in three dimensions of three flaps of identical surfaces, reproducing the geometry of the flaps of a cardiac valve in the closed position of the artery, this weaving being carried out with filaments of fibers of biocompatible synthetic textile material.

With such an embodiment it is possible to impart to each flap 2, directly during production, the mechanical characteristics necessary for its good strength, both during systole and under diastolic pressure, and simultaneously ensuring a perfect and optimum finish of the contact edges of said flaps.

According to another modified embodiment of the invention, not shown in the accompanying drawings, it is also possible to produce an aortic or mitral cardiac valve prosthesis by carrying out the shaping of the flaps 2 by sheathing a textile membrane disposed flat on a corresponding mold, then by carrying out the cutting out bending said flaps and the securement and if desired the thermofixation of the membrane.

According to another modified embodiment of the invention, not shown in the accompanying drawings, the shaping of the flaps 2 can be carried out by slight preliminary mechanical deformation of the selvedge zone of a textile membrane in the direction of a corresponding counter shape, then by application, to the deformations, of a heat exchange fluid. The heat exchange fluid used can be a gaseous fluid, steam, or other liquid fluid. The production of the flaps 2 directly in the selvedge region permits joining the edge of the flaps 2 to be obtained with the edge of the textile membrane. Thus, after deformation, no portion of the membrane is separated from the textile membrane at the deformations of the flaps 2, such that any risk of degradation of the membrane at this point, following cutting out, is avoided. The result obtained is particularly stable dimensionally and mechanically. Moreover, in such a case, the upper securement ring can be omitted, such that the obtained valve has an even greater similarity to a natural valve.

It is also possible to carry out the shaping of the flaps 2 by application of the selvedge zone of a textile membrane against a counter-form by suction through said counter-form, a thermosecurement of the flaps obtained being carried out by the supply of hot air or gas drawn through the textile membrane in the counter-form.

Thus the filamentary and fibrous structure of the textile membrane undergoes deformation by shaping, which promotes a free movement and better distribution of the different points of the membrane, thereby limiting concentrations of stress.

In the case of shaping with slight preliminary mechanical deformation, this mechanical deformation can be effected by means of a die moving the portions of the membranes in the direction of corresponding recesses of the counter shape, the final deformation and thermofixation being then carried out by circulation of a heat exchange fluid, after withdrawal of the die or the like.

In the case of the use of a liquid heat exchange fluid, the latter is projected under a certain pressure against the selvedge region of the textile membrane, which then matches the counter-form. In this embodiment, it is of course necessary to ensure the circulation of the heat exchange fluid.

According to another characteristic of the invention, it is also possible to carry out the shaping of the flaps 2 solely by use of a heat exchange fluid pressing the edge region of the textile material against a counter shape and having a temperature slightly greater than the vitreous transition temperature of the textile used.

Finally, according to the another characteristic of the invention, in the case of production of the flaps 2 directly in the edge region of a textile membrane, a free edge of this region preferably comprises a woven or knit edge avoiding raveling of said edge. Such a procedure is particularly important, because it permits avoiding any ultimate or subsequent treatment of the edge, which could have the result of modifying the mechanical characteristics of the membrane at the edge, or a modification of the thickness of the membrane at this point.

Thanks to the invention, it is possible to produce an aortic or mitral cardiac valve prosthesis that can be easily implanted, by suturing or by intermediate expansible mechanical elements remaining in place, or the like, and having a structure with rigidity against slight flexure, favorable to constraining bending fatigue and associated with a high rigidity and tension, favorable to resisting membrane stress.

The structure of the textile membrane used permits optimum imitation of the behavior of the original valve, namely the radial and circumferential stresses, with a coupling between the two. The compliance of the valve of textile material thus corresponds to that of the natural valve.

Moreover, the different processes for production permit obtaining a valve having a geometry identical to that of the human valve, hence conforming to hemodynamism. In particular, the quasi equality of length between the sum of the radii forming the two free edges of each flap 2, and the corresponding circular segment, permits guaranteeing one of the conditions of closure of the valve during the diastolic phase.

Moreover, the provision of the lower circular skirt, as well as if desired the upper tubular ring, permits either avoiding eventual use of a frame, such that the flow is not disturbed by direct stitching of the two cylindrical elements onto the artery with an optimum orientation relative to flow, or envisaging an implantation by use of a clamping or holding device in place by expansion of the stent type, or by means of an endoscopic suturing device, even for implantation without disturbance of blood flow.

Of course, the invention is not limited to the embodiment described and shown in the accompanying drawings. Modifications remain possible, particularly as to the construction of the various elements or by substitution of technical equivalents, without thereby departing from the scope of protection of the invention.

The invention claimed is:
1. A process for the production of an aortic or mitral cardiac valve prosthesis, comprising:
    shaping flaps (2) by pressing an edge zone of a textile membrane against a counter-form by applying suction of a first fluid through said counter-form so that the flaps are formed with shapes corresponding to a structure of said counter-form; and thermofixing the flaps obtained in said shaping step by drawing a second fluid through the textile membrane into the counter-form, the second fluid being sufficiently hot to thermofix the textile membrane, wherein said thermofixing step follows said shaping step, and wherein the textile membrane is of the type formed by an assembly mode selected from the group consisting of i) woven, ii) non-woven in the form of assembled fibers, and iii) non-woven obtained by autofibrillation of a membrane by drawing and knitting.

2. The process according to claim 1, wherein the first fluid of said shaping step is a liquid heat exchange fluid, and wherein the first fluid is projected at a pressure against the edge zone of the textile membrane to press the textile member against the counter-form such that the textile member matches the counter-form.

3. The process according to claim 1, wherein the second fluid is air or gas.

4. The process according to claim 1, wherein the textile membrane is in the form of a tubular element.

5. The process according to claim 1, wherein the shaping step further includes a slight preliminary mechanical deformation of the edge zone in a direction of the counter-form.

6. The process according to claim 5, wherein the slight preliminary mechanical deformation is effected by a die moving the portion of membranes in a direction of corresponding recesses of the counter-form.

7. The process according to claim 1, wherein the first fluid, in the shaping step, presses the edge zone against the counter-form.

8. A process for the production of an aortic or mitral cardiac valve prosthesis, comprising:

shaping flaps of the valve prosthesis by pressing an edge zone of a textile membrane against a counter-form by applying suction of a first fluid through said counter-form so that the flaps are formed with shapes corresponding to a structure of said counter-form; and thermofixing the flaps obtained in said shaping step by drawing a hot second fluid through the textile membrane into the counter-form, said thermofixing step following said shaping step, and wherein the textile membrane is of the type formed by an assembly mode selected from the group consisting of i) woven, ii) non-woven in the form of assembled fibers, and iii) non-woven obtained by autofibrillation of a membrane by drawing and knitting.

9. The process according to claim 8, wherein the first fluid in said shaping step is a liquid, and wherein the liquid first fluid is projected at a pressure against the edge zone of the textile membrane to press the textile member against the counter-form such that the textile member matches the counter-form.

10. The process according to claim 8, wherein the second fluid is air or gas.

11. The process according to claim 8, wherein the textile membrane is in the form of a tubular element.

* * * * *